United States Patent
Yoon et al.

(10) Patent No.: US 10,845,359 B2
(45) Date of Patent: Nov. 24, 2020

(54) METHOD FOR ANALYZING ACTIVATION STATE OF SIGNALING PATHWAY AND METHOD FOR SELECTING PERSONALIZED MEDICINE USING SAME

(71) Applicant: KOREA ADVANCED INSTITUTE OF SCIENCE AND TECHNOLOGY, Daejeon (KR)

(72) Inventors: Tae-Young Yoon, Daejeon (KR); Hong Won Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/321,813

(22) PCT Filed: Oct. 30, 2014

(86) PCT No.: PCT/KR2014/010299
§ 371 (c)(1),
(2) Date: Dec. 23, 2016

(87) PCT Pub. No.: WO2015/186870
PCT Pub. Date: Dec. 10, 2015

(65) Prior Publication Data
US 2017/0205394 A1    Jul. 20, 2017

(30) Foreign Application Priority Data
Jun. 3, 2014   (KR) .................. 10-2014-0067701

(51) Int. Cl.
| G01N 33/50 | (2006.01) |
| G01N 21/64 | (2006.01) |
| G01N 33/58 | (2006.01) |
| G02B 21/00 | (2006.01) |
| G01N 21/78 | (2006.01) |
| G01N 33/543 | (2006.01) |

(52) U.S. Cl.
CPC ..... G01N 33/5011 (2013.01); G01N 21/6428 (2013.01); G01N 21/78 (2013.01); G01N 33/5041 (2013.01); G01N 33/543 (2013.01); G01N 33/582 (2013.01); G02B 21/00 (2013.01); *G01N 2021/6439* (2013.01); *G01N 2800/52* (2013.01)

(58) Field of Classification Search
CPC .......... G01N 33/5011; G01N 21/6428; G01N 33/582; G01N 2800/52
See application file for complete search history.

(56) References Cited

U.S. PATENT DOCUMENTS

| 2008/0020409 A1 | 1/2008 | Pawlak et al. |
| 2009/0035792 A1 | 2/2009 | Singh et al. |
| 2011/0071042 A1 | 3/2011 | Kim et al. |
| 2014/0113309 A1 | 4/2014 | Yoon |
| 2014/0256649 A1* | 9/2014 | Haura ............... G01N 33/57407 514/19.3 |

FOREIGN PATENT DOCUMENTS

| CN | 103608677 | 2/2014 |
| JP | 2009-052942 | 3/2009 |
| JP | 2010-533842 | 10/2010 |
| JP | 4706026 | 6/2011 |
| JP | 4955391 | 6/2012 |
| JP | 2014-512537 | 5/2014 |
| KR | 10-2012-0119989 | 11/2012 |
| WO | 2005-031309 | 4/2005 |
| WO | 2012-144859 | 10/2012 |
| WO | 2012-144861 | 10/2012 |
| WO | 2013-036064 | 3/2013 |
| WO | 2013-165065 | 11/2013 |

OTHER PUBLICATIONS

Jain et al. Probing cellular protein complexes using single-molecule pull-down. Nature. vol. 473. p. 484-489 (Year: 2011).*
Gazdar. Personalized Medicine and Inhibition of EGFR Signaling in Lung Cancer. N Engl J Med. Sep. 3, 2009; 361(10): 1018-1020. (Year: 2009).*
Lanzerstorfer et al. Quantification and Kinetic Analysis of Grb2-EGFR Interaction on Micro-Patterned Surfaces for the Characterization of EGFR-Modulating Substances. PLoS One 9(3): e92151. p. 1-10 (Year: 2014).*
Douglass et al. Single-Molecule Microscopy Reveals Plasma Membrane Microdomains Created by Protein-Protein Networks that Exclude or Trap Signaling Molecules in T Cells. Cell, vol. 121, 937-950, Jun. 17, 2005 (Year: 2005).*
Dwane et al. Tools used to study how protein complexes are assembled in signaling cascades. Bioengineered Bugs 2:5, 247-259; Sep./Oct. 2011 (Year: 2011).*
Sohn et al. A Method for Analyzing Protein-Protein Interactions in the Plasma Membrane of Live B Cells by Fluorescence Resonance Energy Transfer Imaging as Acquired by Total Internal Reflection Fluorescence Microscopy. Methods Mol Biol. 2010 ; 591: 159-183 (Year: 2010).*
Jain et al. Single molecule pull-down for studying protein interactions. Nat Protoc. ; 7(3): 445-452. (Year: 2011).*
Q. Shi et al., "Single-cell proteomic chip for profiling intracellular signaling pathways in single tumor cells", Proceedings National Academy of Sciences, vol. 109, No. 2, Dec. 27, 2011, pp. 419-424.
Q. Zhou et al., "Development of IGF Signaling Antibody Arrays for the Identification of Hepatocellular Carcinoma Biomarkers", PLOS One, vol. 7, No. 10, Oct. 11, 2012, p. e46851.
H. Lee et al., "Real-time single-molecule co-immunoprecipitation analyses reveal cancer-specific Ras signalling dynamics", Nature Communications, vol. 4, Feb. 19, 2013, p. 1505.
EPO, The Extended European Search Report of EP 14894116.4 dated Jan. 10, 2018.
Hongwon Lee and Tae-YoungYoon, "Single molecule diagnostic method to reveal cancer-related EGFR signaling", Korean Physical Society, Verbal announcement, Oct. 30, 2013.

(Continued)

*Primary Examiner* — Taeyoon Kim
(74) *Attorney, Agent, or Firm* — Lex IP Meister, PLLC

(57) ABSTRACT

The present invention relates to a method for analyzing the activation state of a signaling pathway in a cell or tissue separated from a subject through real time single molecule protein-protein interaction analysis, and a method for selecting a personalized medicine or predicting a therapeutic efficacy to a medicine using the same.

3 Claims, 15 Drawing Sheets

(56) References Cited

OTHER PUBLICATIONS

HongWon Lee et al., "Single Molecule Diagnostic Method to Reveal Cancer-Related EGFR Signaling", Biophysical Journal, vol. 106, Issue 2, Supplement 1, p. 224a, Jan. 28, 2014.

Hongwon Lee et al., Network of EGFR signaling revealed by real-time single-molecule co-IP, Verbal announcement, Feb. 15, 2014.

McNeely, Patrick M et al., "Structure-function studies with G protein-coupled receptors as a paradigm for improving drug discovery and therapeutic development" Biotechnol J. Dec. 2012 ; 7(12): 1451-1461.

H-W, Lee et al., "Real-time single-molecule co-immunoprecipitation analyses reveal cancer-specific Ras Signalling dynamics", Nature Communications, vol. 4, No. 1505, ncomms 2507, pp. 1-9, 2013.

Ankur Jain et al., "Single molecule pull-down for studying protein interactions", Nature Protocols, vol. 7, pp. 445-452(2012), Feb. 9, 2012. doi: 10.1038/nprot.2011.452.

Chen, Minzhang et al., Chinese Internal Medicine Oct. 31, 1999 (preface only).

Wu, Bingquan et al., "Mechanism and Blocking of Tumor Metastasis", Spread of Cancer Basic and Clinical Research, Jun. 30, 2005 (preface only).

SIPO, Search Report of CN 2014800808134 dated Jul. 27, 2020.

\* cited by examiner

[Fig. 1]
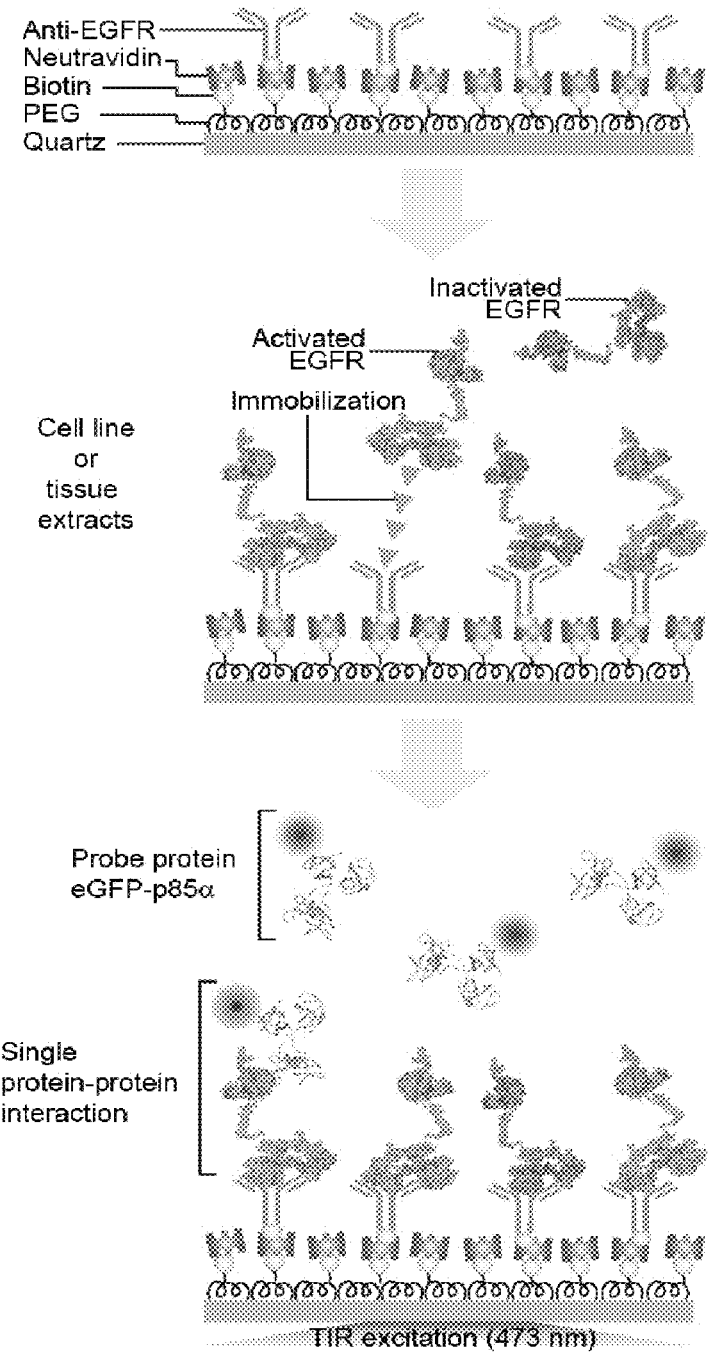

[Fig. 2]
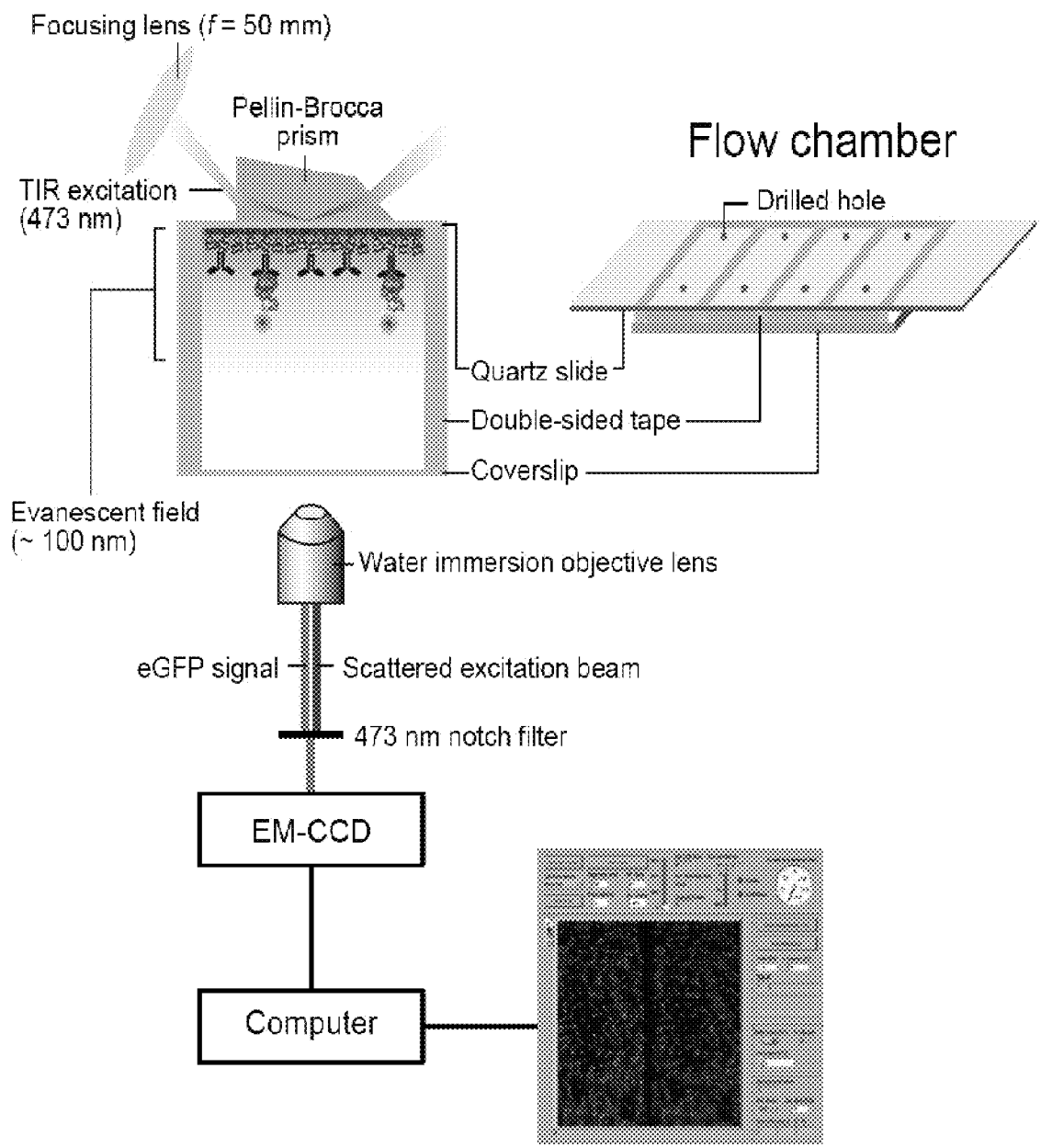

[Fig. 3]
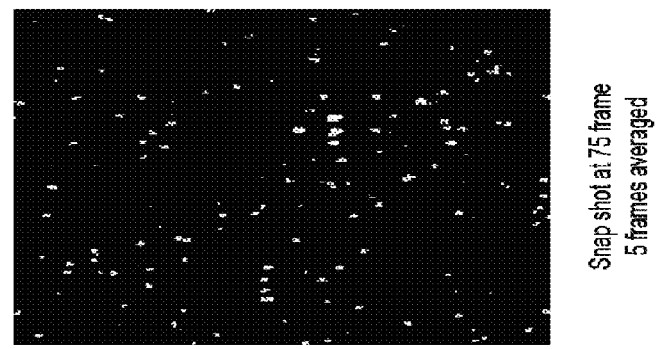
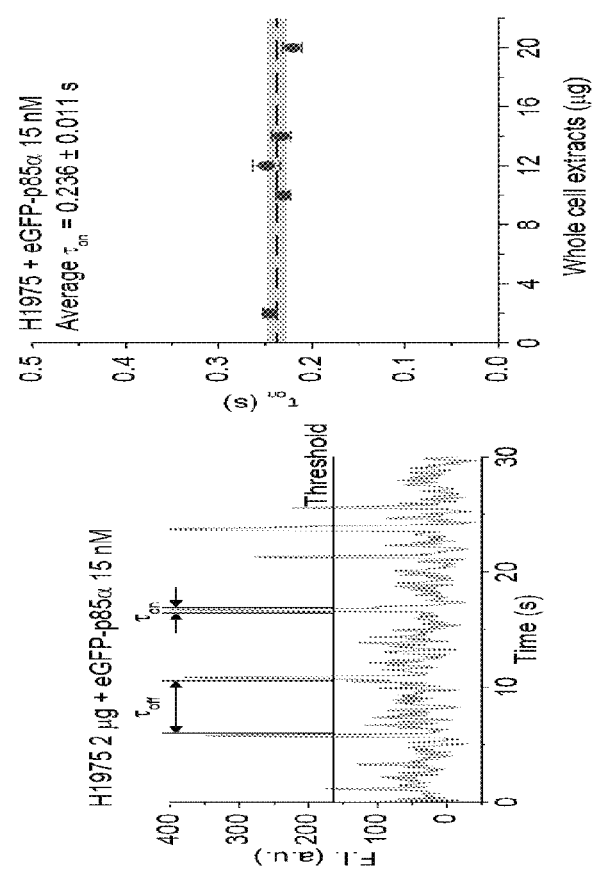

[Fig. 4]
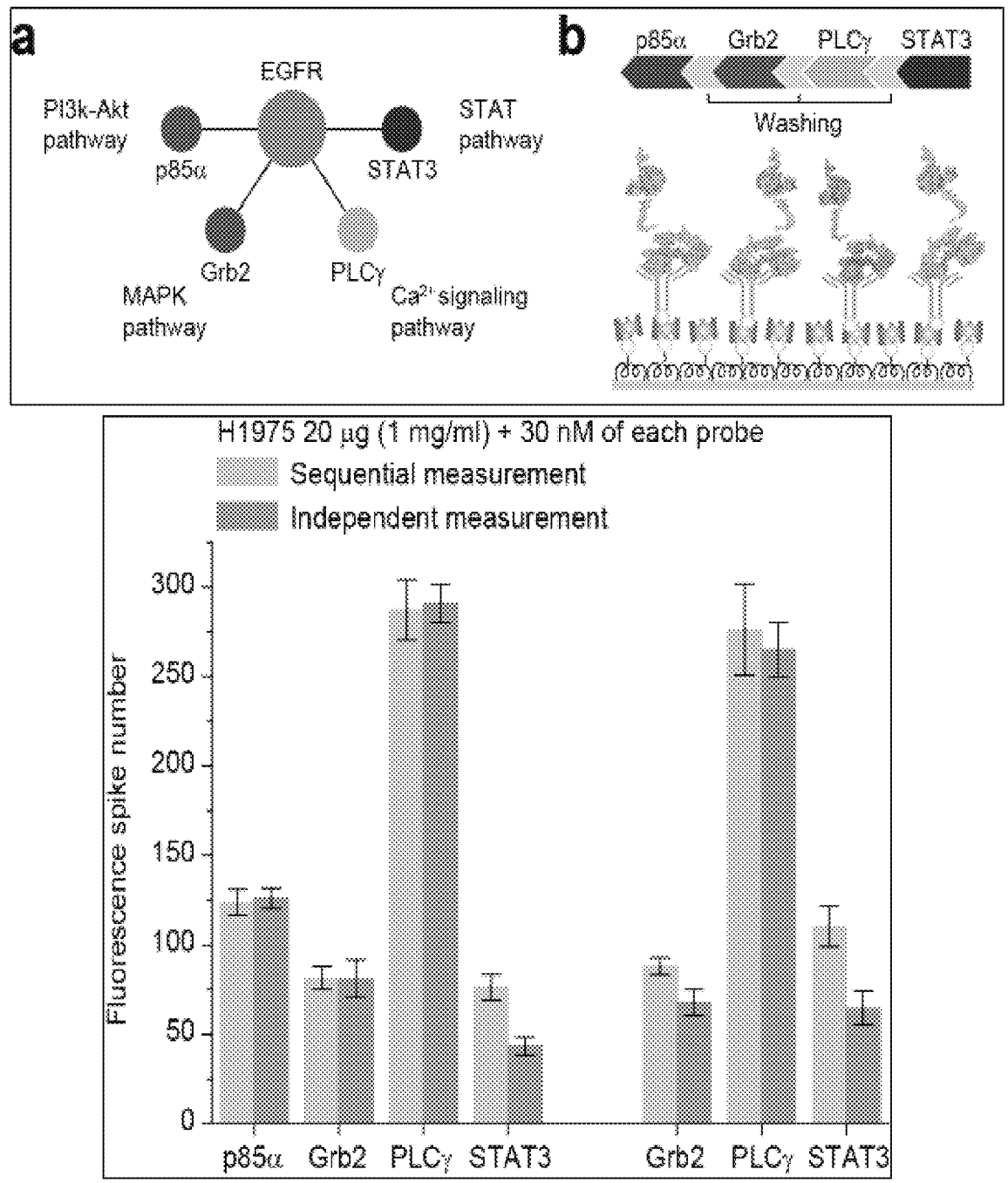

[Fig. 5]
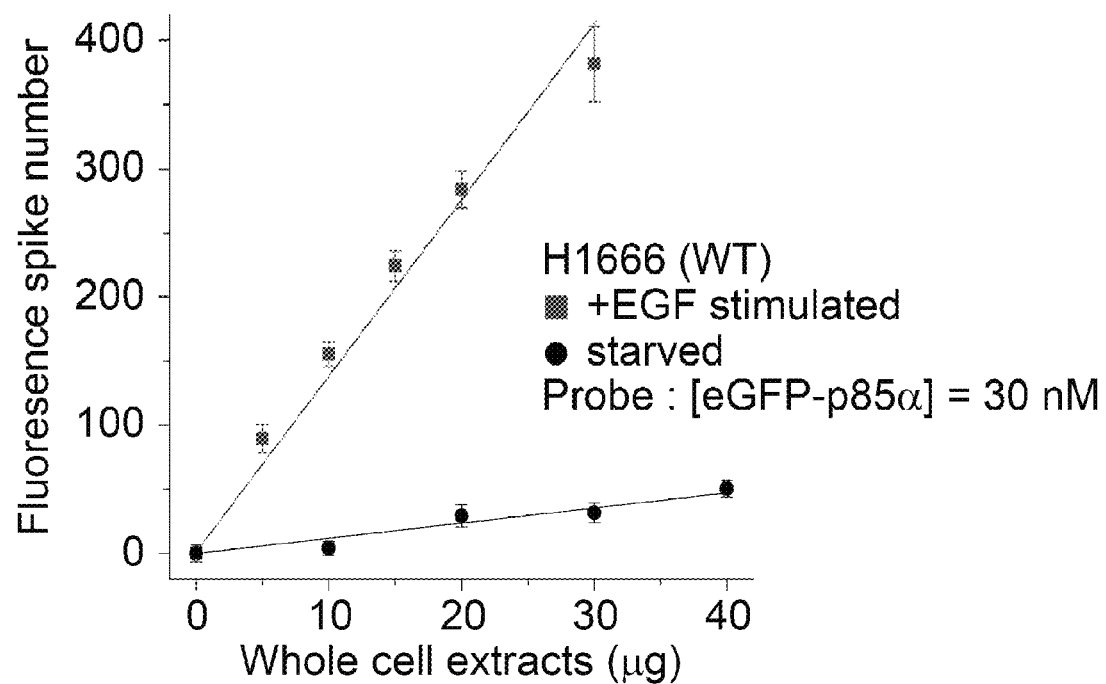

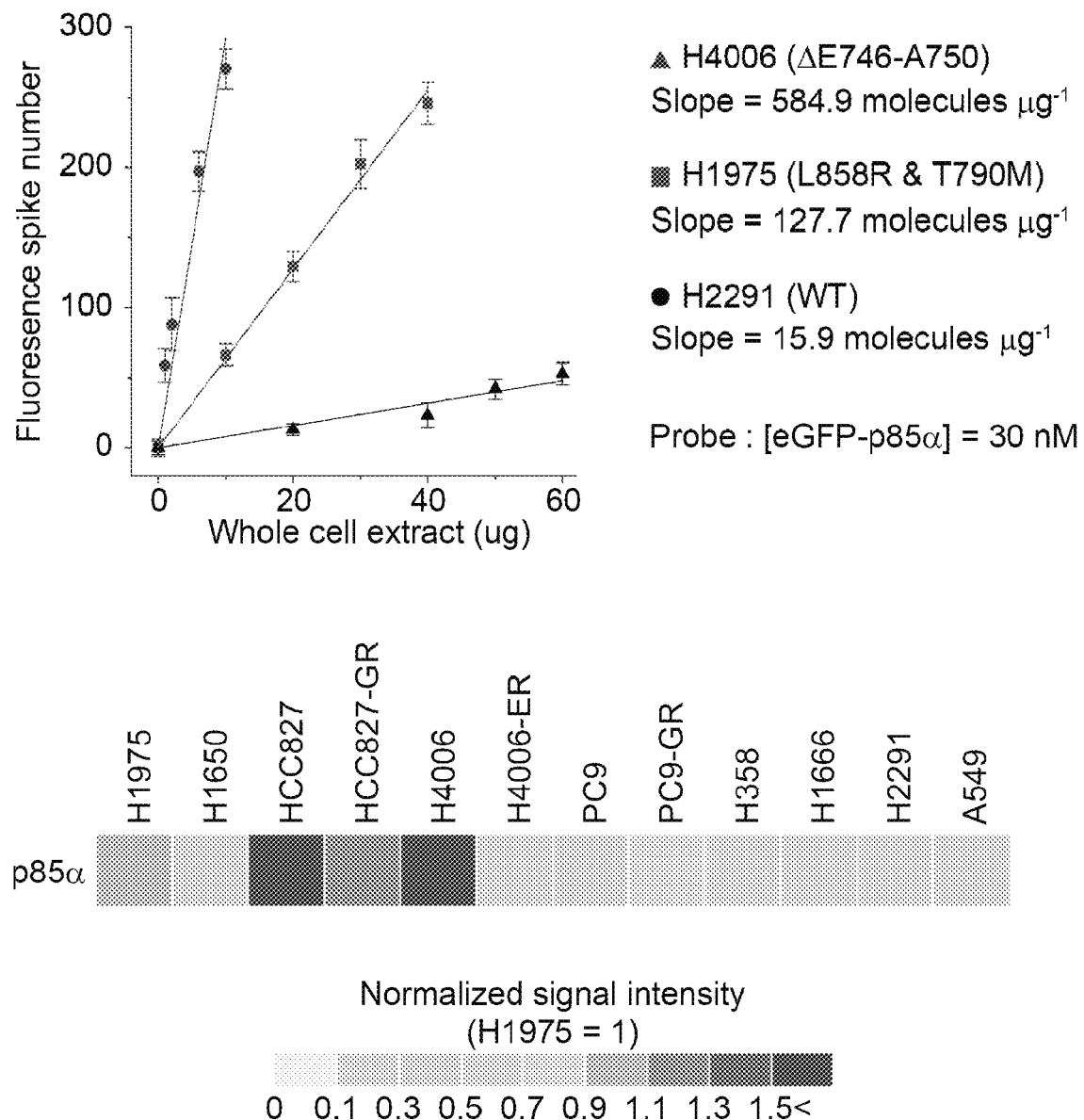
[Fig. 6]

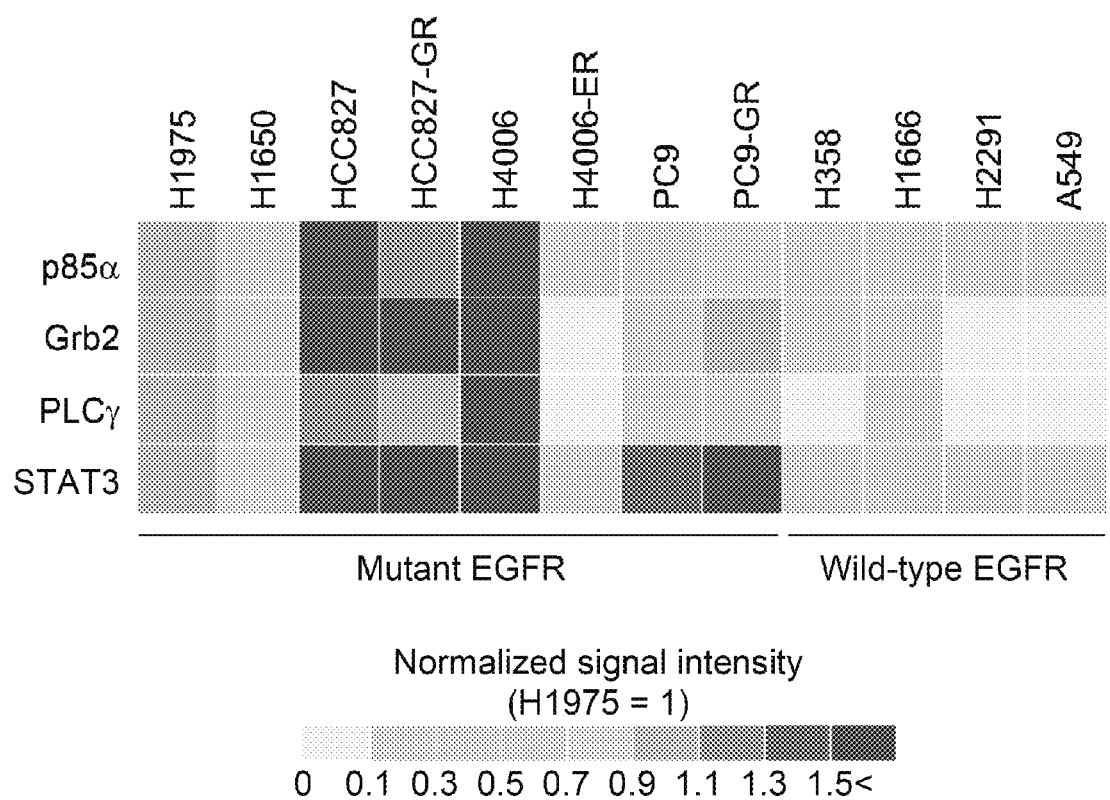
[Fig. 7]

[Fig. 8]
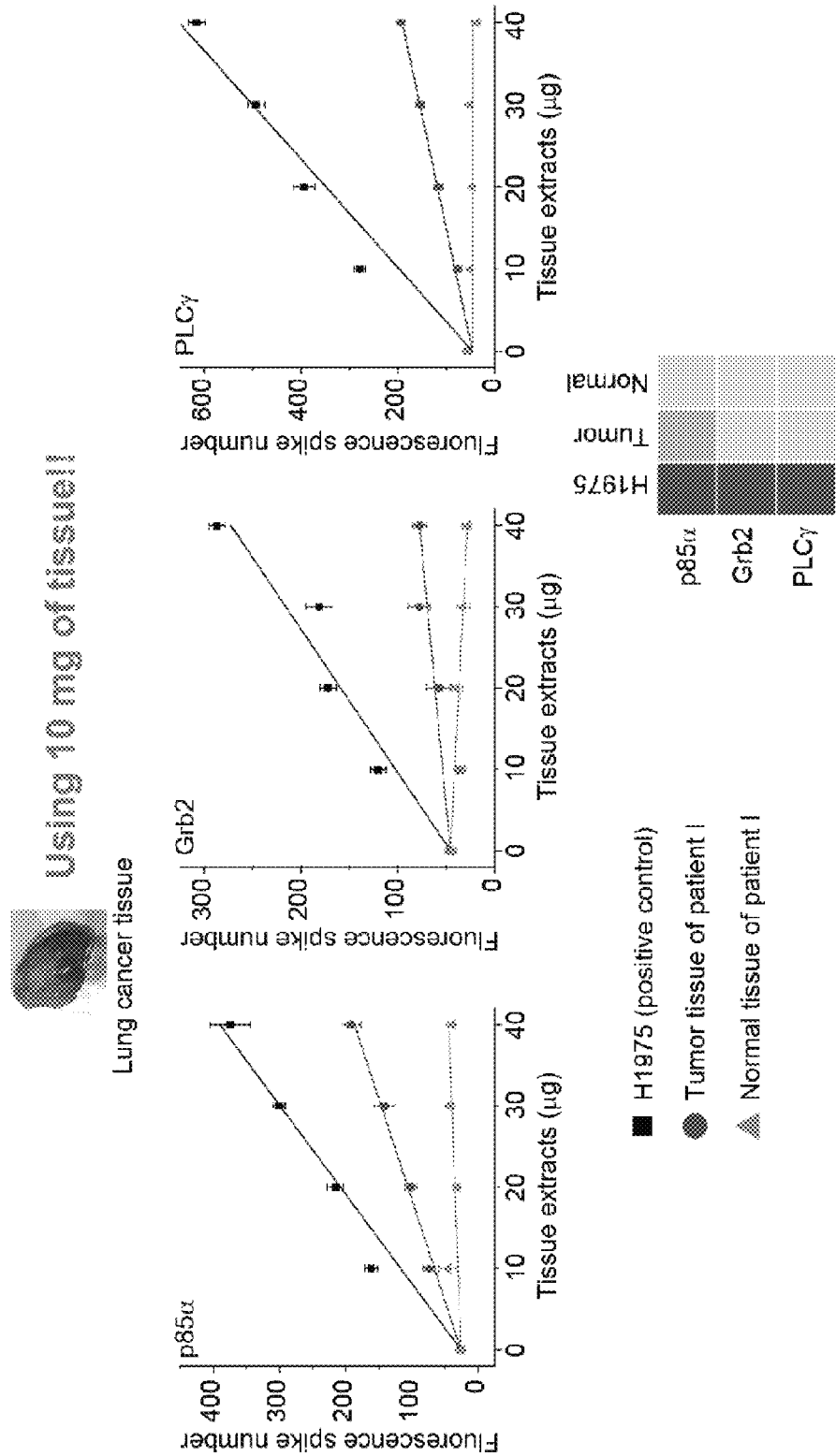

[Fig. 9]
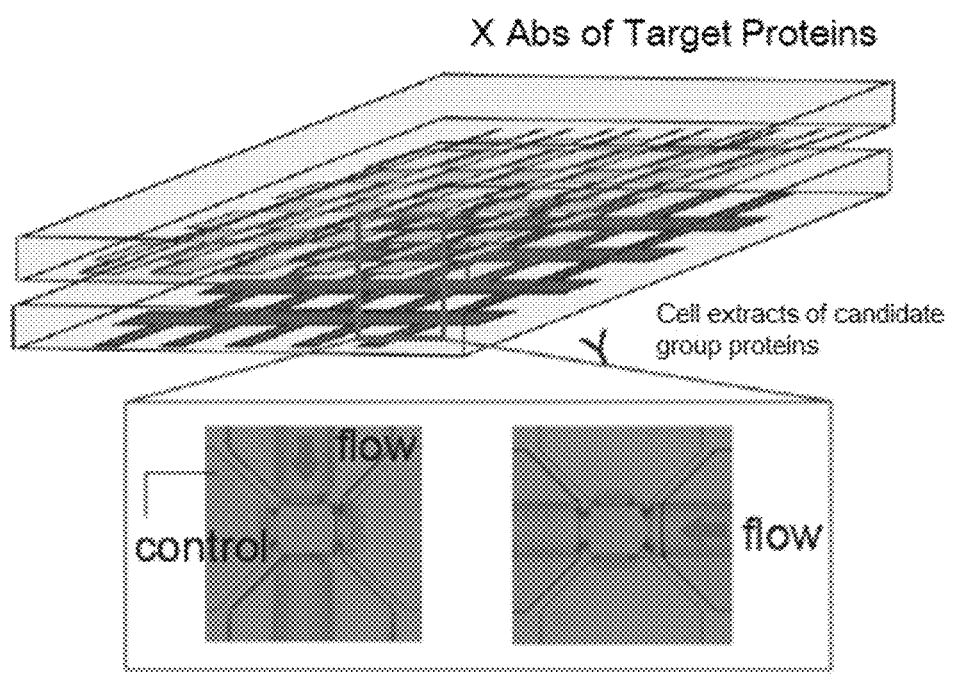

[Fig. 10]
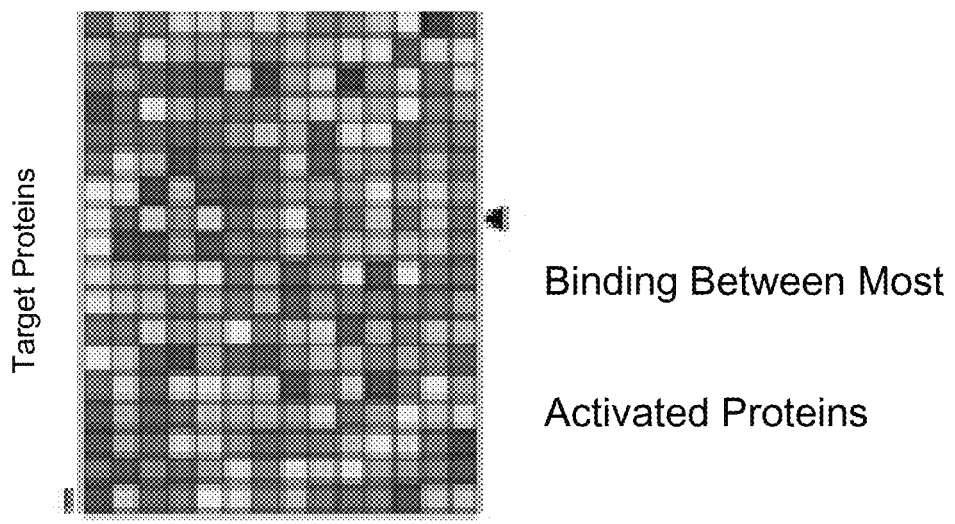

[Fig. 11]
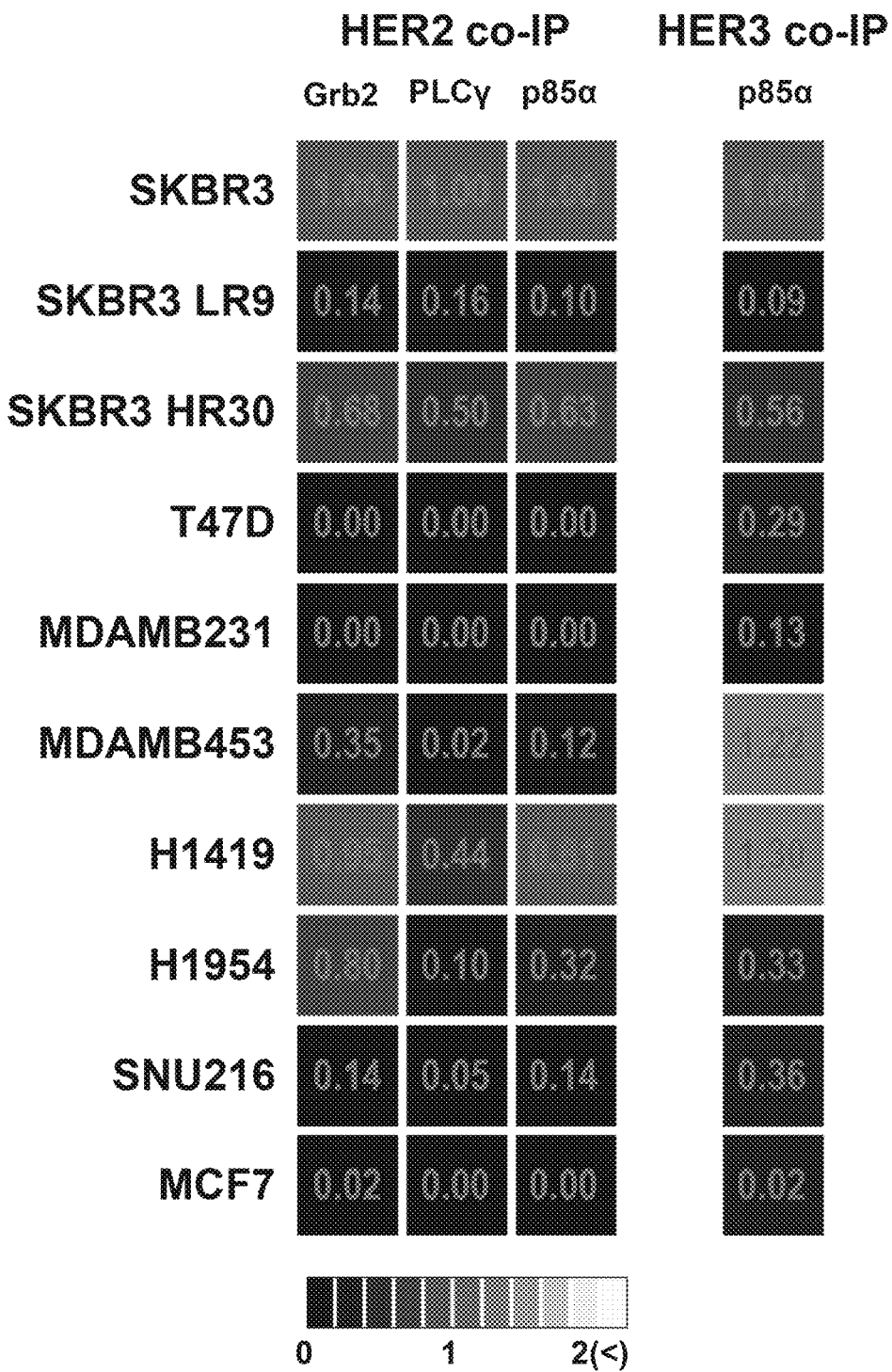

[Fig. 12]
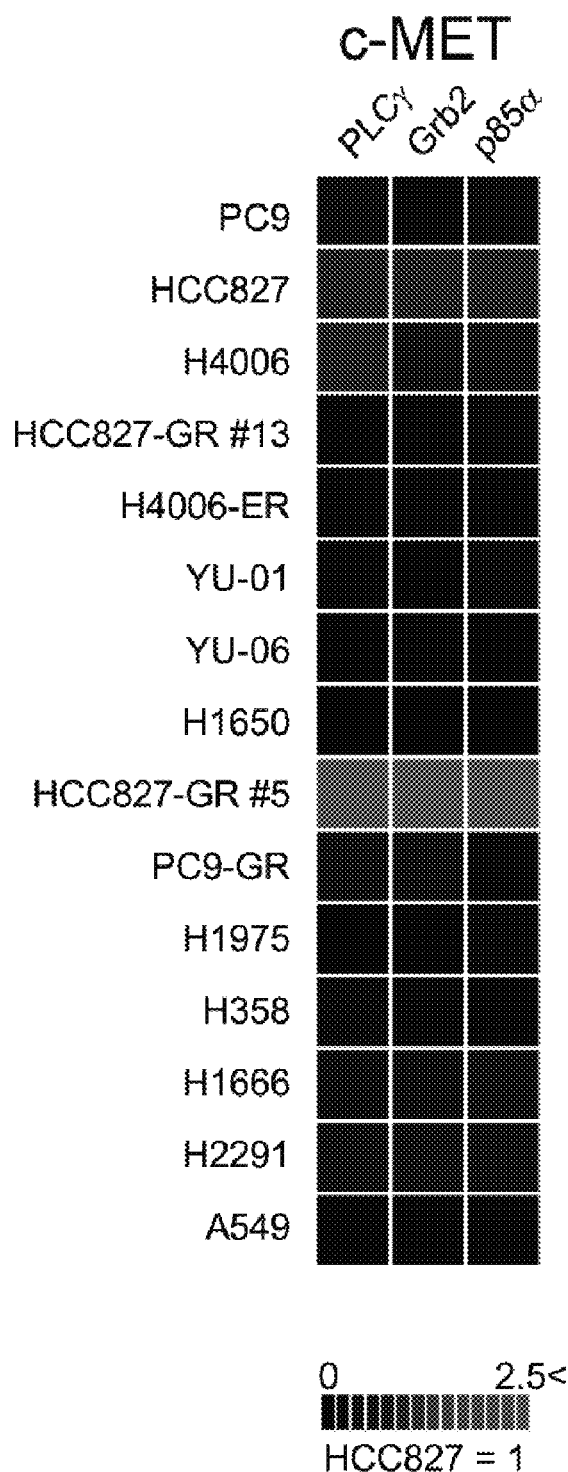

[Fig. 13a]
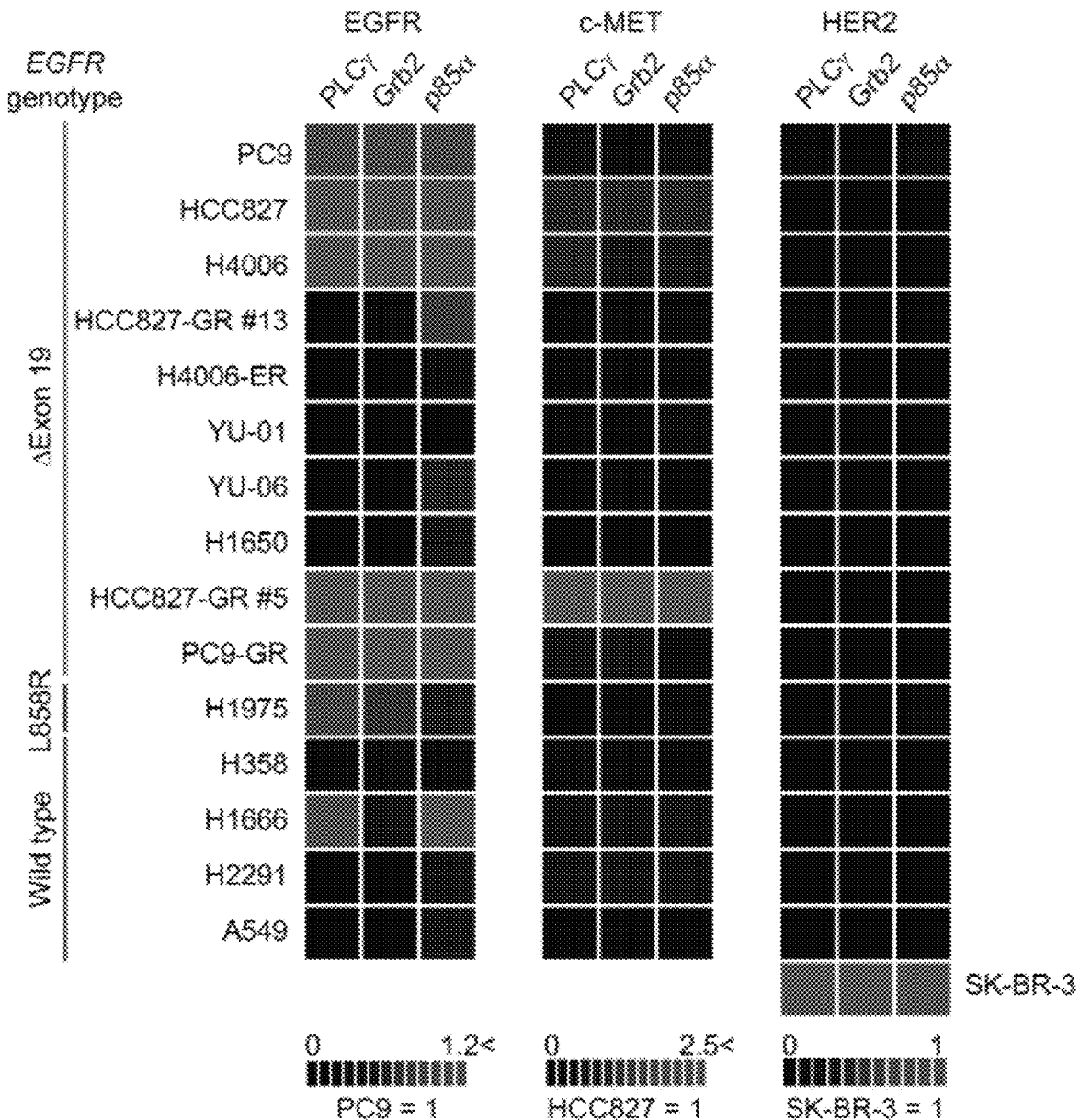

[Fig. 13b]
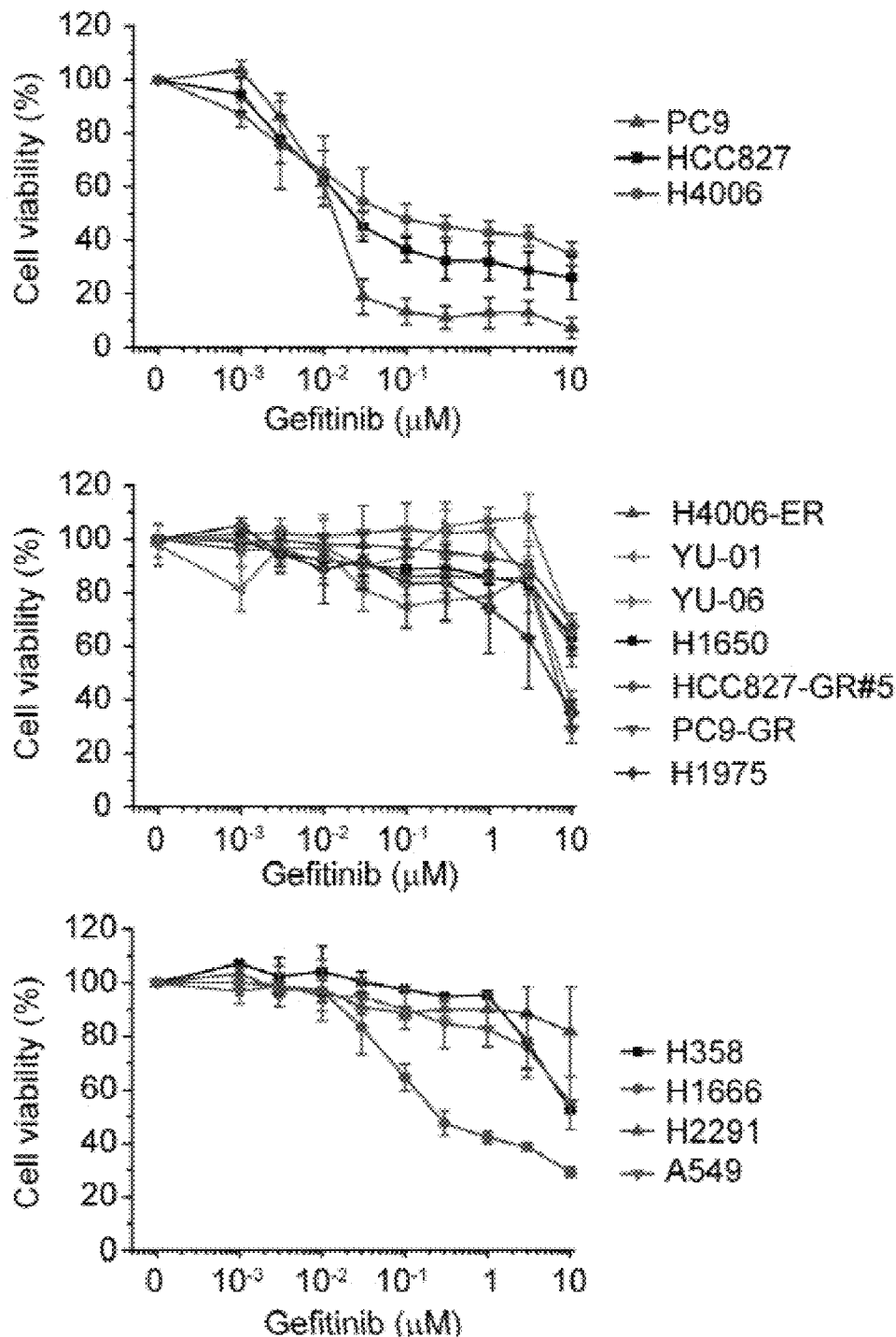

[Fig. 13c]
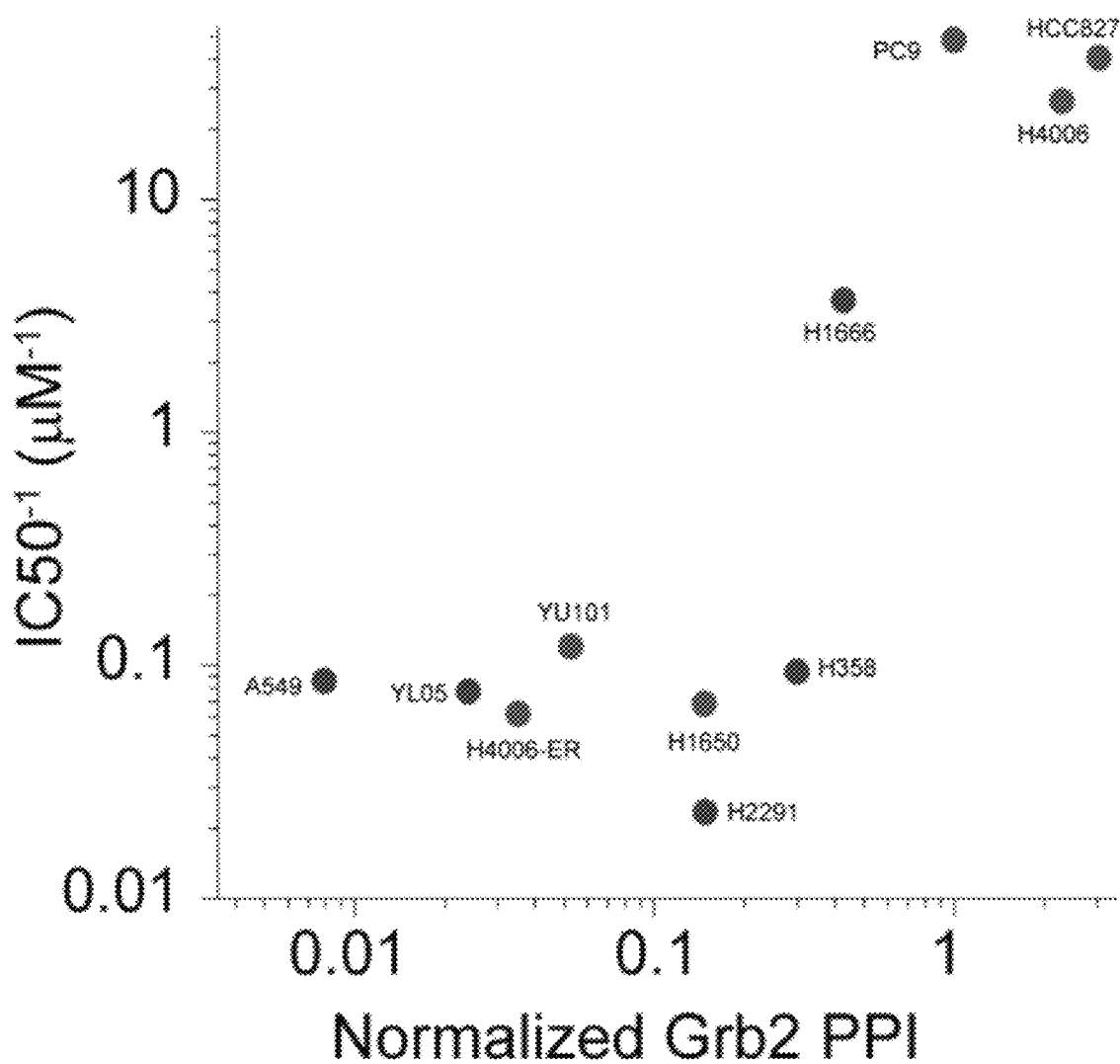

METHOD FOR ANALYZING ACTIVATION STATE OF SIGNALING PATHWAY AND METHOD FOR SELECTING PERSONALIZED MEDICINE USING SAME

TECHNICAL FIELD

The present invention relates to a method for analyzing the activation state of a signaling pathway in cells or tissues separated from a subject through real time single-molecule protein-protein interaction analysis, and a method for selecting a personalized medicine or predicting a therapeutic efficacy to a medicine using the same.

BACKGROUND ART

Recently, personalized diagnosis, prognosis prediction and treatment of diseases have been mainly focused on genomic profiling. However, causes of specific diseases including cancer are due to abnormal activity of cells constituting the human body, and more particularly, abnormal interactions between various proteins that constitute and regulate cells. Thus, the observation of only the protein through gene-based analysis does not provide much guidance. In actual, patients with the same genetic characteristics based on gene profiling may have different susceptibility to a target anticancer drug, and their prognosis may also vary. The analysis of protein-protein interaction at a single-molecule level can provide more accurate information on how a signaling network in cells is changed, and the progression and characteristics of a specific cancer and a treating method thereof.

Recently, a personalized diagnosis and researches for personalized medicines considering characteristics of an individual patient have been conducted by introducing personal gene profiling. However, as described above, since a trait of a disease is determined by protein-protein interaction mediated cell activities, a network formed by protein interactions needs to be studied for more accurate understanding relative to a piecemeal approach of analyzing each protein at a gene level. To fully understand a life phenomenon, understanding of signaling at molecular and interactive network levels is essential. For example, even a patient having the same genetic mutation may exhibit a different reaction to the same target medicine because the cell signaling is based on complex protein-protein interactions. The same cancer protein may be expressed from different signaling pathways.

The accurate analysis of the protein-protein interaction will be an important basis for diagnosis of a disease, evaluation of prognosis, and development of a medicine. The conventional arts verified the interaction of the proteins based on a method of measuring the activity and understanding the interaction. For instance, a method of identifying amino acid residues or atoms related with the interaction at an atom level by using an X-ray crystallography and the like, a method of verifying a binary interaction between two proteins by using a yeast two-hybrid system and the like, and a method of determining a complex interaction through immunoprecipitation and mass spectrometry have been used. In addition to these in-vitro methods, a fluorescence resonance energy transfer (FRET) method and a bimolecular fluorescence complementation (BiFC) method as in-cell analysis methods have been also used.

However, in the case of a chromatography, because proteins are purified and analyzed, it is difficult to identify an interaction between proteins at a single-molecule level similar to an actual cellular environment in which other proteins and the like coexist. In the case of the yeast two-hybrid system, the accuracy of the analysis may vary according to an effect on the transcription activity depending on the expression of the hybrid protein in the cell. The FRET method is a method using fluorescent transition to an adjacent part and has a disadvantage in that the success rate is low because a reliable binding between proteins is indicated only when the fluorescent transition occurs. Particularly, when the binding between the proteins occurs by a weak binding for a short period of time, their inaccurate measurement has been continuously reported as a major drawback.

Accordingly, there has been a great demand for a novel method capable of finding and screening a personalized target medicine by accurately analyzing the interaction between the proteins and predicting a pathway of a disease in a complex environment.

Throughout this specification of the present invention, numerous papers and patent documents are referenced and their citations are indicated. The disclosures of the cited papers and patent documents are entirely incorporated to this specification by reference in this specification and the extent of the art to which the present invention pertains and the contents of the present invention will be more clearly described.

DISCLOSURE

Technical Problem

In view of the drawbacks set forth in the background, the inventors have developed a method for analyzing an activation state of a signaling pathway in cells or tissues based on an analysis method capable of simultaneously analyzing protein-protein interaction at a single molecular level between a target protein and other proteins in the signaling pathway in real time and a method for selecting a personalized medicine using the same.

Therefore, an object of the present invention is to provide a method for analyzing an activation state of a signaling pathway in cells or tissues separated from a subject.

Another object of the present invention is to provide a method for selecting a personalized medicine.

Yet another object of the present invention is to provide a method for predicting a therapeutic reactivity to a medicine.

Other objects and advantages of the present invention are more apparent by the detailed description, claims, and drawings of the present invention below.

Technical Solution

According to an aspect of the present invention, there is provided a method for analyzing an activation state of a signaling pathway in cells or tissues separated from a subject including the following steps:

(a) immobilizing a first protein in the signaling pathway separated from the subject on a substrate by treating the substrate with an extract of cells or tissues including the first protein;

(b) inducing formation of a complex of the first protein and a second fluorescence-labeled protein by supplying to the substrate the second fluorescence-labeled protein that interacts with the first protein; and (c) analyzing interaction between the first protein and the second protein based on a fluorescent signal of a fluorescent label of the second protein, and an activation state of the signaling pathway.

The inventors have developed a method for analyzing an activation state of a signaling pathway in cells or tissues based on an analysis method capable of simultaneously analyzing protein-protein interaction between a target protein and other proteins in the signaling pathway in real time, and a method for selecting a personalized medicine using the same.

Hereinafter, the present invention will be described in detail.

(a) Immobilizing First Protein on Substrate

In step (a), the first protein in the signaling pathway is immobilized on the substrate by treating the substrate with the extract of cells or tissues including the first protein.

According to an exemplary embodiment of the present invention, the immobilization of the first protein may be achieved by immobilizing the first protein to an anti-first protein antibody which is pre-immobilized on the substrate. In this case, it is preferred that an epitope of the first protein to which the antibody binds is distant apart from a binding site of the first protein to which the second protein binds by a predetermined distance.

According to an exemplary embodiment of the present invention, the substrate is a quartz slide coated with polyethylene glycol.

The cell or tissue including the first protein is a normal cell or a normal tissue, but may be an abnormal cell or tissue.

According to an exemplary embodiment of the present invention, the extract of the cell or tissue is an extract of a cancer cell or a cancer tissue. The present invention may reduce time and efforts by performing an analysis by using a cell or tissue extract obtained by lyzing the cancer cell or cancer tissue separated from a subject (for example, a cancer patient) without a complicated pretreatment process. The cell extract may be a cell stock concentrate, or a diluted cytoplasmic stock solution or diluted cell stock solution.

For the cytolysis, a physical method, a chemical method, an enzymatic method, and the like may be used without limitation.

According to an exemplary embodiment of the present invention, in order to remove the first protein which is not immobilized on the substrate, a washing process before performing step (b) is performed. The washing may be performed by using a general washing buffer (for example, PBS).

According to an exemplary embodiment of the present invention, the first protein is a membrane protein.

According to an exemplary embodiment of the present invention, the membrane protein is a receptor. In this case, the present invention may determine a signaling pathway that is being activated by analyzing an interaction between a receptor which is a starting point of the signaling pathway and various types of proteins interacting with the receptor.

The receptor may be receptor tyrosine kinases, a Toll-like receptor, and a G protein-coupled receptor, but is not limited thereto.

According to an exemplary embodiment of the present invention, the receptor tyrosine kinases is selected from the group consisting of an epidermal growth factor receptor (EGFR), a human epidermal growth factor receptor 2 (HER2), a human epidermal growth factor receptor 3 (HER3), a human epidermal growth factor receptor 4 (HER4), and a hepatocyte growth factor receptor (HGFR, c-MET).

According to an exemplary embodiment of the present invention, when the first protein is the receptor tyrosine kinases, the second protein, which will be described in detail below, may be selected from the group consisting of $p85\alpha$, STAT3, Grb2 and PLC$\gamma$. For example, when the first protein is the EGFR, the second protein may be selected from the group consisting of $p85\alpha$, STAT3, Grb2 and PLC$\gamma$, when the first protein is the HER2 or the HGFR, the second protein may be selected from the group consisting of $p85\alpha$, Grb2 and PLC$\gamma$, and when the first protein is the HER3, the second protein may be $p85\alpha$.

(b) Inducing Formation of Complex Between First Protein and Second Fluorescence-Labeled Protein In step (b), the second fluorescence-labeled protein as a protein interacting with the first protein is supplied to the substrate to induce formation of a complex of the first protein and the second fluorescence-labeled protein.

According to an exemplary embodiment of the present invention, the second protein is a protein located downstream of the first protein.

According to an exemplary embodiment of the present invention, the second protein may be supplied to the substrate in a form contained in the cell extract. For example, the cell extract obtained by lyzing a cell that expresses the second protein as a protein located downstream of the first protein in a fluorescence-labeled form may be supplied to the substrate. In order to obtain the cell extract including the second fluorescence-labeled protein, the second fluorescence-labeled protein may be expressed in the cell by a genetic modification of the cell. For example, a polynucleotide coding full-length ORF or some domains of the second protein is introduced into a vector coding the fluorescent gene to prepare a recombinant vector, and then an appropriate host cell (for example, a mammalian cell) is transformed by the recombinant vector to express the second fluorescence-labeled protein. As for the transformation method, electroporation, plasmid fusion, calcium phosphate ($CaPO_4$) precipitation, calcium chloride ($CaCl_2$) precipitation, stirring using silicon carbide fiber, *agrobacterium*-mediated transformation, PEG, dextran sulfate, lipofectamine, and dry/inhibition-mediated transformation, and the like may be used. As another example, the second protein may be fluorescent-labeled by a physicochemical method.

The fluorescent label may be, for example, a green fluorescent protein (GFP), a yellow fluorescent protein (YFP), a blue fluorescent protein (BFP), a cyan fluorescent protein, and the like.

According to the present invention, when the cell extract including the second protein is supplied to the surface of the substrate attached with the first protein, the first protein on the surface of the substrate interacts with the second protein in a manner similar to the intracellular environment where the second protein and other proteins coexist. This means that the analysis method according to the present invention may observe the protein-protein interaction under the same condition as the intracellular environment. That is, the interaction between the first protein and the second protein may be analyzed in the same environment as the intracellular environment by detecting the fluorescent signal of a predetermined wavelength band labeled in the second protein. In the present invention, since the first protein and the second protein interact with each other and are adjacent proteins in the signaling pathway, the activation state of the intracellular signaling pathway.

(c) Analyzing Activation State of Signaling Pathway by Analyzing Interaction Between First Protein and Second Protein In step (c), the interaction between the first protein and the second protein, and an activation state of the signaling pathway is analyzed based on a fluorescent signal of a fluorescent label of the second protein.

The analysis of the interaction between the first protein and the second protein may be performed by measuring a fluorescent signal having a predetermined wavelength generated by a fluorescent label provided in the second protein by using an optical apparatus generating a near field. That is, the interaction between the first protein and the second protein may be verified by observing the surface of the substrate by the optical apparatus generating the near field such as a total reflection microscope to analyze the interaction such as a frequency of binding and separation between the first protein and the second fluorescence-labeled protein on the surface of the substrate.

According to an exemplary embodiment of the present invention, the analysis of the interaction between the first protein and the second protein is performed by using a total internal reflection fluorescence microscope. In this case, the fluorescent signal may be measured in real time in the step where the complex between the first protein and the second proteins is formed. Distinguished from the conventional general immune precipitation method, the method of the present invention that combines immune precipitation and fluorescent imaging for analyzing single-molecule protein-protein interaction in real time performs a monomolecular imaging of a non-purified cell or tissue extract in a reaction chamber in real time, and may verify the binding at a single-molecule level in real time.

According to an exemplary embodiment of the present invention, the analysis of the fluorescent signal may integrate and measure a fluorescent signal having a predetermined wavelength represented by the fluorescent label for a predetermined time. That is, when a wavelength change on the surface of the substrate is measured by the total internal reflection fluorescence microscope.

By using the method of the present invention, a signaling pathway that is activated in a cell or tissue separated from a subject including a human subject may be verified (analyzed). In the following Examples, interactions between EGFR that is known to be closely associated with cancer, and its downstream proteins, p85α, STAT3, Grb2 and PLCγ were analyzed by using various cancer cell lines and tissues derived from cancer patients. It was verified that there was a difference in terms of the EGFR activation level for each cell line or between the cancer tissue and the normal tissue (see Experimental Examples 3 and 4). Furthermore, in the following Examples, the interaction between RTKs other than the EGFR and the downstream proteins thereof was analyzed by targeting various cancer cell lines (see Experimental Examples 5 and 6). Such a result exhibits that a signaling pathway which is particularly activated in the cell or tissue separated from each subject may be found by applying the method of the present invention, and exhibits that personalized prognosis prediction and treatment are possible, such as predicting a prognosis of a disease of each subject based on information on the activated state of the analyzed signaling pathway and selecting a suitable medicine (for example, an anticancer agent targeting the activated signaling pathway) each subject.

According to the present invention, the present invention may select one type of protein as the second protein that interacts with the first protein, or also use various types of proteins interacting with the first protein as described in Experimental Example 3 below. For example, in the case of analyzing interaction between the first protein and various types of its downstream proteins (a plurality of types of second proteins), various types of second proteins may be simultaneously or sequentially supplied to the substrate. For example, when the second proteins are sequentially supplied to the substrate, first, after the analysis of the interaction between the supplied second proteins and the first protein is completed, the analyzed second proteins are removed through a washing process, and then a process of supplying other second proteins to the substrate may be performed.

Particularly, according to an exemplary embodiment of the present invention, in the case of sequentially supplying various types of second proteins to the substrate, the method of the present invention further includes, after step (c), step (d) repetitively performing steps (b) and (c) by using a protein (interacting with the first protein), as the second protein, different from the second protein used in analyzing the interaction in steps (b) and (c). In this case, after analyzing the interaction between the second protein and the first protein, an interaction with the first protein may be additionally analyzed by supplying a different type of second protein to the substrate after removing the second protein by performing a washing process. Because the process of immobilizing the first protein on the substrate is performed only once, and the interaction with various types of second proteins may be analyzed, the analysis using only a small amount of sample is possible. It is very advantageous when considering that the extracted amount of a human tissue is very limited and that an amplifying process such as PCR for proteins is not possible.

In the present invention, steps (a) to (c) may be performed by using various types of first proteins and various types of second proteins. That is, the present invention may analyze the interaction between the first protein and the second protein by treating various types of second proteins (candidate proteins, e.g. downstream proteins of the first protein) that interact with the first proteins after immobilizing various types of first proteins (target proteins) on the substrate. For example, after various types of first proteins are immobilized on the substrate to which various types of antibodies are attached, the x-axis and y-axis are set as the first proteins and the second proteins, respectively, and the interactions between the proteins are analyzed based on fluorescent signals. The number of first proteins is adjusted to a parallel line to form microfluidic channels. The microfluidic channels are immobilized on the substrate by using the antibodies according to the number of first proteins. A vertical line allows channels to be formed by the number of second proteins. A double-layered structure may be used, and the second microfluidic channel may be stacked on the top of the first channel to be used as a cross reaction point. Alternatively, the first channel may be applied to be attachable or detachable after installing the second channel. According to the method, a pattern of the interaction due to an independent reaction in an independent chamber may be analyzed. FIG. 9 is a schematic diagram of the interaction analysis method and FIG. 10 illustrates the analysis of an interaction between the first protein and the second protein based on a fluorescent signal. The red signal indicates the binding between the most activated proteins. Through the present invention, a specific signaling pathway (binding between specific proteins) activated in the cell or tissue extracted from each patient may be verified, and as a result, resistance to a drug for each patient may be predicted in advance and a personalized treatment is possible by selecting a target medicine capable of obtaining an optimal therapeutic effect.

Further, the conventional gene profiling focuses on nodes in cell signaling, whereas the present invention focuses on lines connecting the nodes. One joint has many nodes and one higher protein is connected with many lower proteins, and one lower protein is connected with many higher proteins. The present invention can observe comprehensively how one higher protein is converged and branched in the signaling pathway.

According to another aspect of the present invention, the present invention provides a method for selecting a personalized medicine including the following steps:

(a) analyzing an activation state of a signaling pathway in a cell or tissue separated from an individual by using the aforementioned method; and (b) searching a medicine targeting the activated signaling pathway verified in step (a) and selecting the searched medicine as the personalized medicine.

The step (a) that uses the method for analyzing the activation state of the signaling pathway in the cell or tissue separated from the aforementioned subject is already explained above.

In step (b), the medicine targeting the activated signaling pathway is searched based on the analyzed result of step (a). For example, after the method for analyzing the activation state of the signaling pathway in the cell or tissue separated from the aforementioned subject is performed by using various types of first proteins and various types of second proteins, specific signaling pathways that are activated or the binding between the specific proteins in the cell or tissue separated from the subject is verified. Then, a medicine targeting the verified signaling pathways or proteins is searched, and the medicine may be selected as the personalized medicine.

As the method for selecting the personalized medicine in step (b), for example, after the personalized medicine is selected among known medicines targeting the activated signaling pathway verified in step (a) or a test material is treated in a cell line or tissue where the signaling pathway verified in step (a) is activated, the personalized medicine may be selected by a screening process of verifying whether the test material inhibits the activation of the signaling pathway, or whether the candidate drug inhibits the growth of the cell line or tissue, and the like. The test material may use low molecular weight compounds, high molecular weight compounds, nucleic acid molecules (for example, DNA, RNA, PNA and aptamer), proteins, sugars, lipids, and natural materials.

According to an exemplary embodiment of the present invention, the medicine is an anticancer agent.

According to another aspect of the present invention, the present invention provides a method for predicting a therapeutic efficacy to a medicine including the following steps:

(a) analyzing an activation state of a signaling pathway in a cell or tissue separated from the human to predict a therapeutic efficacy to a medicine by using the aforementioned method; and (b) predicting the therapeutic efficacy to the medicine targeting the signaling pathway, based on analysis information on the activation state of the signaling pathway verified in step (a).

In step (a), after the cell or tissue is separated from the predicted human, the activation state of the signaling pathway in the separated cell or tissue is analyzed. The method for analyzing the activation state of the signaling pathway in step (a) is described above and will be not be further explained.

For example, in the case of the cancer treatment, a treatment using an anticancer agent targeting a specific signaling pathway (for example, an EGFR pathway, an HER2 pathway, and the like) is frequently performed. However, the activation degree of the signaling pathway targeted by the anticancer agent is different for each individual, and particularly, when the activation degree of the signaling pathway targeted by the anticancer agent is inactivated or the activation degree is relatively low, it is difficult to obtain the therapeutic effect from the anticancer agent. Accordingly, it is important to predict the therapeutic efficacy to the anticancer agent before administrating the anticancer agent in advance and select appropriate therapeutic methods and drugs. The therapeutic efficacy to the anticancer agent may be predicted in advance by using the method of the present invention.

In step (b), the therapeutic efficacy to a medicine targeting the signaling pathway is predicted based on analysis information on the activation state of the signaling pathway. In Experimental Example 6 below, it is verified that there is a difference in terms of the activation degree in each signaling pathway for every cancer cell lines, and there is also a difference in terms of sensitivity to the anticancer agent targeting the signaling pathway. Through these result, it is verified that the therapeutic efficacy of the subject to the anticancer agent targeting the signaling pathway may be predicted in advance based on the activation information of the signaling pathway analyzed according to the method of the present invention.

According to an exemplary embodiment of the present invention, the medicine is an anticancer agent, and the anticancer agent is a target anticancer agent targeting a specific signaling pathway.

Advantageous Effects

Features and advantages of the present invention are summarized as follows:

(i) The present invention relates to a method for analyzing the activation state of a signaling pathway in a cell or tissue separated from a subject, and a method for selecting a personalized medicine or predicting a therapeutic efficacy to a medicine using the same.

(ii) The method of the present invention is a novel method for personalized diagnosis and medical treatment and can analyze how the target medicine affects the signaling pathway and the patient.

(iii) The present invention can comprehensively understand the signaling pathway by analyzing how the signaling of a specific disease is branched and converged and may be used as a platform for developing a personalized medicine by verifying which signaling is distorted in the entire signaling network. There has been a problem in resistance of cancer tissues to the target anticancer agent, but it is expected that according to the platform, the resistance is predetected and a secondary medicine for the resistance is designed to largely reduce recurrence of the cancer.

DESCRIPTION OF DRAWINGS

FIG. 1 illustrates a schematic diagram of an experiment used in Experimental Example below.

FIG. 2 illustrates a structural diagram of an observation system used in Example below.

FIG. 3 illustrates a result for single-molecule fluorescence observation and quantification.

FIG. 4 illustrates intensities of fluorescent signals according to an exchange among an EGFR, its downstream proteins and a probe protein.

FIG. 5 illustrates intensities of fluorescent signals of an activated EGFR and an inactivated EGFR.

FIG. 6 illustrates a degree of interaction between EGFR and p85α in 12 types of lung cancer cell lines.

FIG. 7 illustrates relative intensities based on the degree of the interaction between EGFR and the lower protein thereof in each cell line.

FIG. 8 illustrates an activation degree of EGFR in a cancer tissue and a normal tissue derived from the same patient.

FIG. 9 illustrates binding between target proteins (first proteins) and candidate proteins (second proteins).

FIG. 10 illustrates fluorescent signals of the signaling pathway measured by the method of FIG. 9.

FIG. 11 illustrates relative intensities of the interactions between HER2 and lower proteins thereof and between HER3 and lower proteins thereof in each breast cancer cell line.

FIG. 12 illustrates relative intensities based on the degree of the interaction between HGFR(c-MET) and the lower protein thereof in each lung cancer cell line.

FIG. 13A illustrates relative intensities based on the degree of the interaction between EGFR and the lower protein thereof, between the HGFR and lower proteins thereof, and between HER2 and lower proteins thereof in each cell line.

FIG. 13B illustrates a reactivity to Gefitinib as an EGFR target anticancer agent of respective cell lines.

FIG. 13C illustrates integrally the degree of the interaction with Grb2 of the EGFR illustrated in FIG. 13A and sensitivity to the target anticancer agent of respective cell lines measured in FIG. 13B.

BEST MODE

Hereinafter, the present invention will be described in more detail through Examples. These Examples are just to describe the present invention in more detail and it is apparent to those skilled in the art that the scope of the present invention is not limited to these Examples.

EXAMPLES

Example 1. Preparation of Extract Buffer 150 mM NaCl, 1 mM EDTA and 1% (vol/vol) triton X-100 were dissolved in distilled water to prepare a lysis buffer. A 2× concentrated stock buffer was prepared and stored in a refrigerator at 4° C. Before making a cell extract, the lysis buffer was diluted by using the 2× concentrated stock buffer at the final concentration described above. In this case, a protease inhibitor (Sigma P8340, Sigma) and a phosphatease inhibitor (P5726, Sigma) were respectively added to inhibit functions of the protease inhibitor and the phosphatease inhibitor in the cell extract. The respective inhibitors per 5 mg/ml of the cell extract were diluted at a concentration of 1:100. An amount of the extract was determined so that the final concentration of a cell line extract or a tissue extract was 5 to 10 mg/ml. Generally, when 5×10$^6$ cells were dissolved in 200 µl of the lysis buffer, a total of protein amount of about 6 to 10 mg/ml was made, and when 20 mg of a human lung tissue was dissolved in 1 ml of the lysis buffer, a total of protein amount of about 10 to 13 mg/ml was made.

Example 2. Preparation of Target Protein (First Protein)

A target protein means a target protein to analyze characteristics through the present invention. In the following Experimental Example, EGFR, HER2, HER3 or HGFR as one of oncoproteins was used as the target protein. A native protein without a purifying process using a fluorescent label or Tag and the like was immediately extracted and used from a cell line or a tissue sample of an actual patient. In order to prepare the target protein from the cell line, a process of putting an appropriate amount of lysis buffer prepared in the Example 1 in the cell line and homogeneously releasing the aggregated cell lines by using a pipette of 100 to 200 µl was repeated. All of the reactions proceeded in a cold block on ice. Thereafter, the prepared sample was dissolved for 30 minutes on ice. In order to prepare the target protein from the tissue, the tissue was finely cut by using operating scissors so that the cell lysis may easily occur by increasing a cross-sectional area contacting the tissue and the lysis buffer. Herein, an appropriate amount of lysis buffer was put and homogeneously released by using a pipette of 1 ml. Thereafter, the tissue was finely grinded by using a mechanical homogenizer (IKA, cat. No. 3737000). After the reaction for 30 minutes, the tissue was maintained at 4° C. for 10,000 g×10 minutes and centrifuged. A sunken part (pellet) was removed and only a solution part (supernatant) was taken. In the solution part, a target protein to be observed and other proteins are included. Thereafter, during all of the experimental processes, the extract was stored in the ice to allow the protein to be stored in the most stable state. A total protein amount of the prepared extract of the cell or tissue was measured by using a DC protein assay kit (Bio-Rad, #500-0111) or a protein quantitative kit.

Example 3. Preparation of Probe Protein (Second Protein)

A probe protein used a partner protein interacting with the target protein as a protein labeled with a fluorescent protein. The entire probe protein (full length ORF) or a predetermined domain was put in an eGFP vector (pEGFP-C1 vector, Clontech) having a good fluorescent characteristic to prepare a plasmid in the eGFP-probe protein form. The plasmid was injected to a HEK293 cell by an electroporation method to express the probe protein and then the cell was obtained and stored at −80° C. A process of preparing the probe protein was performed in the same manner as the process of preparing the target protein in Example 2. However, since the probe protein was attached with the eGFP, in order to measure the amount of expressed probe protein, the amount of expressed fluorescent protein was measured by using a fluorometer (Perkin Elmer Enspire 2300) to quantify how much the probe protein was included.

Example 4. Immobilization of Target Protein

A measurement was performed by using a total internal reflection fluorescence microscope (TIRFM). To this end, polyethylene glycol (PEG) coating and biotin-PEG coating for capturing were performed on a substrate made of a quartz slide. For washing, a chamber made on the substrate was continuously washed twice by using 200 µl of PBS and neutravidin was injected in the chamber by 50 µl per chamber. The neutravidin protein was attached to the surface by binding to biotin on the surface of the substrate. The neutravidin protein was reacted at room temperature for 5 minutes and then was washed by the above method. An antibody for the target protein (in the case of EGFP, EGFR Ab-10, clone 111.6 biotin-labeled mouse monoclone antibody; Thermo Scientific, #MS-378-B) was injected into the substrate and immobilized. Thereafter, the extract including the target protein (the cell or tissue extract) was injected into the substrate (concentration range: 0.1 mg/ml to 10 mg/ml; reaction time: at least 10 to 30 minutes). Thereafter, the extract was continuously washed twice by using 200 µl of PBS (FIG. 1).

Example 5. Probe Protein Injection & Detection

A cell extract including the fluorescence-labeled probe protein was injected to the substrate immobilized with the target protein of Example 4 at an appropriate concentration. In the case of using a total internal reflection fluorescence microscope, 50 nM eGFP is a threshold concentration value capable of performing normal observation. The threshold concentration value may be changed according to observation optical equipment and a substrate form (the last step of FIG. 1). Thereafter, the substrate was observed by using the total internal reflection fluorescence microscope. In order to observe the protein interaction, a signal generated for a short time was measured by using an exposure time of 50 ms. FIG. 2 is a structural diagram of an observation system including a substrate, a microscope, and an analysis program.

The substrate injected with the probe protein was recorded in real time for about 5 seconds (100 frames with 0.05 sec exposure time) by using a fluorescence microscope. The number of the probe proteins that were bound to the target protein on the surface in a predetermined frame was observed by using a single-molecule fluorescent protein observation algorithm. Generally, one image is generated by averaging 3 to 10 frames and the number of single-molecule signals is measured by analyzing the image. In the process of measuring the frame number, kinetics of the interaction between two proteins are first analyzed through real time single-molecule protein-protein interaction analysis (the first panel of FIG. 3). When it is measured how long the two proteins are bound to or separated from each other, the average frame number is determined. In the experiment, 5 frames (250 ms) were measured by the most appropriate average frame number (the second panel of FIG. 3) and a frame skipped by a unit of 25 frames. For example, a total of four data points was formed by averaging 1 to 5 frames, and thereafter, 25 to 29 frames, 50 to 54 frames, and 75 to 79 frames.

The most appropriate average frame starting point was found. This was performed based on a point representing the largest difference between a positive control group (a surface immobilized with the target protein) and a negative control group (a surface immobilized with only a primary antibody). A 75-th frame was measured from the most appropriate time (the third panel of FIG. 3). Five data were collected by moving positions in one chamber to be prepared as one data by calculating an overall average value and a standard deviation. The preceding process was repeated while changing the concentration of the target protein extract to compare the activated degree of the target protein in various samples.

Example 6. Exchange of Probe Protein

The present invention has an advantage of simply applying various probe proteins (second proteins) to one prepared substrate. A protein such as EGFR has various lower signaling pathways and thus measuring a plurality of signaling pathways plays an important role in identifying a biological information delivery. Furthermore, the target protein needs to be prepared only once and has an advantage of using a small amount of cell or tissue extract. A process of exchanging the probe protein will be described below. After the measurement of one probe protein is completed, the above measurement process was repeated by removing the remaining protein in the chamber through a washing process and then injecting other probe proteins.

Meanwhile, a possible hinderance in the observation of the next probe protein due to the previous probe protein is examined. When the next probe protein is introduced, the remaining first probe protein is also separated by competitive binding (the last panel of FIG. 4). The result exhibits that one target protein and a plurality of probe proteins may be measured for a short time even through exchange of the probe proteins.

Experimental Example 1. Activation State Analysis of EGFR

In the present invention, in an epidermal growth factor receptor (EGFR), classified as the most famous carcinogenic membrane protein among receptor tyrosine kinases (RTKs), was used to study the suitability of the experiment and to collect actual data. An experimental process was performed according to the method described above.

A cell line NCI-H1666, known as a lung cancer cell line expressing normal EGFR, was used. The EGFR is phosphorylated by a ligand called EGF to interact with a lower signal protein. In the present experiment, an eGFP-p85α was used as a probe protein which was formed by binding of eGFP with p85α, a subunit of phosphoinositide 3-kinases (PI3K), a representative lower signal protein of the EGFR. First, a H1666 cell line was cultivated after dividing into two groups. The H1666 cell line was starved for 24 hrs by using a serum-free media. In this case, since the media has no nutrient, the cell stops from growing, it is known that the EGFR is in an unphosphorylated state. Thereafter, EGF of 100 ng/ml was treated for 3 minutes in the cells of one group. This is an external factor that provides an activation signal to the EGFR to turn the EGFR into a phosphorylated state. After the cell lines in two groups were gathered, the EGFR state of the two cell lines was observed.

As illustrated in FIG. 5, in the cell line with the phosphorylated EGFR, the slope of the graph is steep, but in the inactivated cell line, a relatively gradual slope is observed (FIG. 5). The result exhibits that the slope value measured by the present invention may be used as an indicator showing how much the target protein in the cell is activated.

Experimental Example 2. Analysis of EGFR Activation Degree of Various Non-Small-Cell Lung Cancer Cell Lines Using p85α

The EGFR states of a total of 12 non-small-cell lung cancer (NSCLC) cell lines (H1975, H1650, HCC827, H4006, H358, H1666, H2291 and A549 obtained from American Type Culture Collection; HCC827-GR, H4006-ER, PC9 and PC9-GR obtained from the Yonsei University Hospital) were quantified by using the eGFP-p85α probe protein. Generally, it is known that the EGFR is always present in the activated form through exon 19 deletion mutation or exon 21 point mutation (L858R) to cause the cancer. H1975, H1650, HCC827, HCC827-GR, H4006, H4006-ER, PC9 and PC9-GR among 12 cell lines used in the experiment are cancer cell lines having EGFR mutation and the rest of four cell lines are cancer cell lines having normal EGFR.

A reactivity between EGFR and p85α was measured by the method described above to quantify the EGFR state of each cell line. The reactivity of H4006 (exon 19 deletion), H1975 (exon 21 mutation) and H2291 (normal EGFR) cell lines were measured and represented in a graph. As illustrated in the upper panel of FIG. 6, it was verified that the activation degree of EGFR in two different cell lines with the mutated EGFR was higher than the H2291 cell line with the normal EGFR. Further, it was seen that there is a difference in the degree between H4006 and H1975.

With respect to 12 NSCLC cell lines, the activation degree of EGFR was measured to be represented by a heatmap. As illustrated in the lower panel of FIG. 6, a signal generated in the H1975 cell line was normalized to be "1" and the relative values of the signal intensities of the remaining cell lines were obtained.

In the present invention, the intensity of the interaction between EGFR as one kind of RTK and p85α as the lower protein thereof can be measured. Further, when the appropriate antibody is selected, the present invention may be applied to various RTKs in addition to EGFR to measure the signal of the target protein generated in each cell line and the degree of the interaction between the target protein and the probe protein.

Experimental Example 3. Analysis of EGFR Activation Degree of NSCLC Cell Lines Using Four Types of EGFR Lower Proteins The relative signal intensity of the EGFR was analyzed by using a plurality of probe proteins by extending the signal intensity quantified in Experimental Example 2. As illustrated in FIG. 7, the effects of various signaling pathways that originated from the EGFR on each cell line, and the comparison of each cell line may be observed. The result confirms that the present invention may aid in selecting an anticancer agent targeting a specific signaling pathway. Similarly, the result of measuring the relative signal value of each cell line based on the H1975 cell line is illustrated in FIG. 7.

Experimental Example 4. Characteristic Analysis of Human Cancer Tissue

A difference between a human cancer tissue (lung cancer) and a normal tissue was verified by using all of the aforementioned methods. The lung cancer tissue was obtained from the Eulji University Hospital. An experiment was performed by using a tissue extract of 10 mg. In the cancer tissue and the normal tissue, the difference in terms of activation degree of the EGFR was measured by using the present invention and compared relative to H1975.

As illustrated in the lower end of FIG. 8, it can be verified that there is a large difference in activation degree of EGFR between the cancer tissue and the normal tissue. The result confirms that an appropriate treatment suitable for each patient may be provided by inspecting an unknown tissue extracted from each patient and verifying a particular signaling pathway that is activated.

Experimental Example 5. Activation State Analysis of Various RTKs

In order to show that the present invention can be applied to other RTKs in addition to the EGFR in the above Experimental Examples, the experiment for HER2, HER3 and HGFR (c-MET) was performed. As the probe protein of HER2 and HGFR, the target protein, Grb2, PLCγ, and p85α were used, and as the probe protein of HER3 the target protein, p85α was used.

In the case of HER2/HER3, in a total of 10 breast cancer cell lines SKBR3, T47D, MDAMB231, MDAMB453, H1419, H1954 and MCF7 obtained from American Type Culture Collection; SKBR3 LR9, SKBR3 HR30 and SNU21 obtained from the Seoul University Hospital), the activation degree of HER2 and HER3 was measured to be expressed by a heat map (FIG. 11). FIG. 11 is a result illustrating signal intensities of remaining cell lines by a relative value after normalizing the signal measured in a SKBR3 cell line to be 1.

In the case of HGFR, in a total of 15 NSCLC cell lines (HCC827, H4006, H1650, H1975, H358, H1666, H2291 and A549 obtained from American Type Culture Collection; PC9, HCC827-GR #13, H4006-ER, YU-01, YU-06, HCC827-GR #5 and PC9-GR obtained from the Yonsei University Hospital), the activation degree was measured, and similarly, the signal intensities of the remaining cell lines are illustrated by a relative value after normalizing the HCC827 cell line to be 1 (FIG. 12).

The results of FIGS. 11 and 12 exhibit that the present invention is not limited to the specific RTK and also can be applied to all receptors including the RTKs.

Experimental Example 6. Analysis of Correlation Between Protein-Protein Interaction (PPI) and Drug Reactivity With respect of a total of 15 NSCLC cell lines, a correlation between protein-protein interaction (PPI) and a reactivity to Gefitinib as an EGFR target anticancer agent was analyzed by applying the method. The degree of the interaction with Grb2 of the EGFR illustrated in FIG. 13A and sensitivity to the target anticancer agent of respective cell lines measured in FIG. 13B were integrally illustrated in FIG. 13C. A horizontal axis of FIG. 13C means that the signaling of EGFR is increased toward the right side and a vertical axis means that sensitivity to the target anticancer agent is increased toward the upper side.

FIG. 13C illustrates that the measured signaling intensity of EGFR has a positive correlation with the sensitivity to the target anticancer agent. The result exhibits that the activation degree of the signaling pathway targeting the target anticancer agent is measured with respect to an unknown test sample by using the present invention to predict the sensitivity to the target anticancer agent in advance.

Although the specific part of the present invention has been described in detail, it is obvious to those skilled in the art that such a specific description is just a preferred embodiment and the scope of the present invention is not limited thereby. Thus, the substantial scope of the present invention will be defined by the appended claims and equivalents thereof.

The invention claimed is:

1. A method of selecting a human subject for administration of an anticancer agent, comprising:
   (i) determining an activation state of a signaling pathway in a cancer cell or cancer tissue separated from a human subject by (a) immobilizing a first protein in the signaling pathway on a substrate by treating the substrate with an extract of cells or tissues separated from the subject including the first protein; (b) inducing an interaction between the first protein and a second fluorescence-labeled protein by supplying to the substrate the second fluorescence-labeled protein that interacts with the first protein; and (c) analyzing interaction between the first protein and the second protein based on a fluorescent signal of a fluorescent label of the second protein, and an activation state of the signaling pathway using a total internal reflection fluorescence microscope, (ii) selecting the subject for administration of an anticancer agent if the cell or tissue is determined to be in the activation state compared to a normal cell or tissue; and (iii) administering the anticancer agent to the selected subject, wherein in step (i)(c), one image is generated by averaging a predetermined number of frames and the number of single-molecule signals is measured by analyzing the image, wherein the predetermined number of frames is obtained according to a duration of binding of the two proteins ($\tau_{on}$) relative to an exposure time required to measure the fluorescent signal, wherein the signaling pathway is one selected from EGFR, HER2, HER3 and HGFR pathway, wherein the anticancer agent is capable of targeting EGFR, HER2, HER3 or HGFR signaling pathway, wherein the first protein is a receptor tyrosine kinase, a Toll-like receptor, or a G protein-coupled receptor, wherein the plurality of the second proteins is a downstream protein of the first protein.

2. The method of claim 1, wherein the fluorescent signal analysis in the step (c) is performed by measuring the fluorescent signal in real time.

3. The method of claim 1, further comprising (d) repeating steps (b) and (c) using a fluorescence-labeled protein that interacts with the first protein but different from the second protein so as to analyze interactions between the first protein and a plurality of the second proteins.

* * * * *